United States Patent
Ninomiya

(10) Patent No.: US 10,019,798 B2
(45) Date of Patent: Jul. 10, 2018

(54) IMAGE PROCESSING APPARATUS AND RECONSTRUCTION CONDITION SETTING METHOD

(71) Applicant: Hitachi, Ltd., Tokyo (JP)

(72) Inventor: Hiroaki Ninomiya, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/309,911

(22) PCT Filed: May 20, 2015

(86) PCT No.: PCT/JP2015/064423
§ 371 (c)(1),
(2) Date: Nov. 9, 2016

(87) PCT Pub. No.: WO2015/186513
PCT Pub. Date: Dec. 10, 2015

(65) Prior Publication Data
US 2017/0148157 A1    May 25, 2017

(30) Foreign Application Priority Data
Jun. 5, 2014    (JP) .................................. 2014-116456

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/5205* (2013.01); *G06T 11/003* (2013.01); *G06T 2207/10081* (2013.01)

(58) Field of Classification Search
CPC ........ A61B 6/032; A61B 5/055; G06T 11/006; G06T 7/0012; G06F 19/321
(Continued)

(56) References Cited

U.S. PATENT DOCUMENTS 7,689,266 B2 *  3/2010  Shinohara ................ A61B 6/00
                                                            378/4
7,970,192 B2 *  6/2011  Boeing .................. A61B 6/032
                                                            378/115
(Continued)

FOREIGN PATENT DOCUMENTS

JP    S63109843 A    5/1988
JP    H10127622 A    5/1998
(Continued)

OTHER PUBLICATIONS

International Search Report dated Aug. 18, 2015 for International Patent Application No. PCT/JP2015/064423.

*Primary Examiner* — Charlotte M Baker

(57) ABSTRACT

An image processing apparatus includes a control unit that reconstructs images by using raw data, a storage unit that stores the raw data, the images, and reconstruction conditions used when the images are reconstructed, in correlation with each other, a display unit; and an input unit that inputs selection of an image on which post-reconstruction will be performed among the images stored in the storage unit and post-reconstruction conditions, by referring to the image displayed on the display unit, in which the control unit receives selection of the image which is input via the input unit, reads selected image reconstruction conditions based on the received selection of the image from the storage unit, calculates comparison information of image quality on the basis of the read reconstruction conditions and post-reconstruction conditions input via the input unit, and displays the calculated comparison information on the display unit.

9 Claims, 10 Drawing Sheets

(51) Int. Cl.
    *A61B 6/03*           (2006.01)
    *A61B 6/00*           (2006.01)
    *G06T 11/00*          (2006.01)

(58) Field of Classification Search
    USPC ........ 382/131, 173, 181, 128, 115; 600/431,
                         600/437, 411, 440, 407; 378/4, 8, 16
    See application file for complete search history.

(56) References Cited

U.S. PATENT DOCUMENTS 9,824,467 B2 *   11/2017   Litvin .................. G06T 11/005
2003/0083561 A1     5/2003   Toth et al.

FOREIGN PATENT DOCUMENTS

| | | |
|---|---|---|
| JP | 2003153893 A | 5/2003 |
| JP | 2003180677 A | 7/2003 |
| JP | 2006025868 A | 2/2006 |
| JP | 2006296646 A | 11/2006 |

* cited by examiner

FIG.9

RECONSTRUCTION CONDITIONS

PATIENT INFORMATION  31

| 20130101 | Taro Hitachi | 12345678 | Head |
| 20130102 | Jiro Hitachi | 12345679 | Chest |
| 20130103 | Hanako Hitachi | 12345680 | Head |

SERIES INFORMATION  32

| 000000000001 | 200 | 2013/01/01 | 10:30:49:82 | Head | 8 |
| 000000000002 | 200 | 2013/01/01 | 10:31:58:29 | Head | 8 |

RECONSTRUCTION PARAMETER  33

FOV                     500
FOV-X,Y                 0.0
Slice thickness         0.10
Start and end locations 0.0 – 50.0
Interval                1.00
filter                  Lung Sharp

PREVIEW IMAGE  38

RECONSTRUCTION START  36

IMAGE PROCESSING APPARATUS AND RECONSTRUCTION CONDITION SETTING METHOD

CROSS-REFERENCE TO RELATED APPLICATIONS

This application is a national phase claiming the benefit of and priority to International Patent Application No. PCT/JP2015/064423, entitled "IMAGE PROCESSING DEVICE AND RECONSTRUCTION CONDITION SETTING METHOD", filed May 20, 2015, which claims priority to Japanese Patent Application No. 2014-116456, entitled "IMAGE PROCESSING DEVICE AND RECONSTRUCTION CONDITION SETTING METHOD", filed Jun. 5, 2014, which are hereby incorporated by reference in their entireties.

TECHNICAL FIELD

The present invention relates to an image processing apparatus which uses measured data (raw data) obtained by a medical imaging apparatus such as an X-ray computed tomography (CT) apparatus or a magnetic resonance imaging (MRI) apparatus for image reconstruction processing, and image reconstruction conditions. Particularly, the present invention relates to a technique of setting reconstruction conditions in post-reconstruction in which reconstruction is performed with reconstruction conditions which are different from conditions set during scanning.

BACKGROUND ART

In the related art, in a medical imaging apparatus, an image used for image diagnosis is obtained by reconstructing raw data. The quality, a rendering range, or the like of the reconstructed image may be insufficient for diagnosis. In a case where the image is insufficient for diagnosis, rescanning is required to be performed, or a post-reconstruction process is necessary. Since a CT image or an MR image includes a plurality of sliced images, if all of the plurality of images are reconstructed through the post-reconstruction process, a long calculation time is necessary, and thus the time for diagnosis is increased.

Meanwhile, a method has been proposed in which an image obtained when scanning is performed with set scanning conditions is presented to an operator before scanning. For example, PTL 1 discloses a method in which a simulation image corresponding to set scanning conditions is generated by using sample image data having a reference value regarding an index of image noise in advance. If the technique disclosed in PTL 1 is used, a simulation image as a result of simulation can be checked before scanning, and thus it is possible to minimize errors in setting of scanning conditions and thus to prevent rescanning.

CITATION LIST

Patent Literature

[PTL 1] JP-A-2004-329661

SUMMARY OF INVENTION

Technical Problem

However, in the method disclosed in PTL 1, the image presented to the operator is a simulation image based on a sample image, and is not generated by using an image of an object which is a scanning target.

PTL 1 does not disclose a post-reconstruction process. PTL 1 does not take into consideration this post-reconstruction process.

The present invention has been made in consideration of the above-described problems, and an object thereof is to provide an image processing apparatus and reconstruction condition setting method, capable of presenting comparison information between an original image and an output scheduled image to an operator when an image is reconstructed through changing of reconstruction conditions.

Solution to Problem

In order to achieve the above-described object, according to the present invention, there is provided an image processing apparatus including a control unit that reconstructs images by using raw data measured by a medical imaging apparatus; a storage unit that stores the raw data, the images, and reconstruction conditions used when the images are reconstructed, in correlation with each other; a display unit that displays an image read from the storage unit; and an input unit that inputs selection of an image on which a post-reconstruction process will be performed among the images stored in the storage unit and post-reconstruction conditions, by referring to the image displayed on the display unit, in which the control unit receives selection of the image which is input via the input unit, reads the selected image reconstruction conditions from the storage unit, calculates image quality comparison information on the basis of the read reconstruction conditions and post-reconstruction conditions input via the input unit, and displays the calculated comparison information on the display unit.

According to the present invention, there is provided an image processing apparatus including a control unit that reconstructs images by using raw data measured by a medical imaging apparatus; a storage unit that stores the raw data, the images, and reconstruction conditions used when the images are reconstructed, in correlation with each other; a display unit that displays an image read from the storage unit; and an input unit that inputs selection of an image on which a post-reconstruction process will be performed among the images stored in the storage unit and post-reconstruction conditions, by referring to the image displayed on the display unit, in which the control unit displays a preview image generated by the image reconstruction unit on the display unit, performs the post-reconstruction process on slices other than a slice of a representative image among selected images in parallel to generation and display of the preview image, performs the post-reconstruction process on the representative image among the selected images by applying the post-reconstruction conditions, and generates the preview image by performing the post-reconstruction process.

According to the present invention, there is provided reconstruction condition setting method to execute a step of reconstructing images by using raw data measured by a medical imaging apparatus; a step of storing the raw data, the images, and reconstruction conditions used when the images are reconstructed, in correlation with each other in the storage unit; a step of selecting an image on which a post-reconstruction process will be performed among the images stored in the storage unit; a step of inputting post-reconstruction conditions; a step of acquiring selected image reconstruction conditions from the storage unit; a step of calculating comparison information of image quality on the basis of the acquired reconstruction conditions and the input post-reconstruction conditions; and a step of displaying the calculated comparison information on a display unit.

According to the present invention, there is provided a reconstruction condition setting method to execute a step of reconstructing images by using raw data measured by a medical imaging apparatus; a step of storing the raw data, the images, and reconstruction conditions used when the images are reconstructed, in correlation with each other in the storage unit; a step of selecting an image on which a post-reconstruction process will be performed among the images stored in the storage unit; a step of inputting a post-reconstruction conditions; a step of performing the post-reconstruction process by applying the post-reconstruction conditions to a representative image among selected images, so as to generate a preview image; a step of displaying the generated preview image; and a step of performing the post-reconstruction process on slices other than a slice of the representative image in parallel to generation and display of the preview image.

Advantageous Effects of Invention

According to the present invention, it is possible to provide an image processing apparatus and a reconstruction condition setting method, capable of presenting comparison information between an original image and an output scheduled image to an operator when an image is reconstructed through changing of reconstruction conditions.

BRIEF DESCRIPTION OF DRAWINGS

FIG. 7 illustrates an example of a reconstruction condition setting screen 3a.

FIG. 9 illustrates an example of a reconstruction condition setting screen 3b.

DESCRIPTION OF EMBODIMENTS

Hereinafter, embodiments of the present invention will be described in detail with reference to the drawings.

First Embodiment

First, with reference to FIG. 1, a description will be made of the entire configuration of an X-ray CT apparatus as an embodiment of an image processing apparatus according to the present invention. An image processing apparatus according to the present invention is not limited to the X-ray CT apparatus 1, and is applicable to various modalities having image processing apparatuses performing an image reconstruction process, such as an MRI apparatus, a PET apparatus, and other medical imaging apparatuses. The present invention is applicable to various image processing apparatuses such as a computer which can read raw data (measured data) stored in a storage device and can perform an image reconstruction process.

Figure 1:
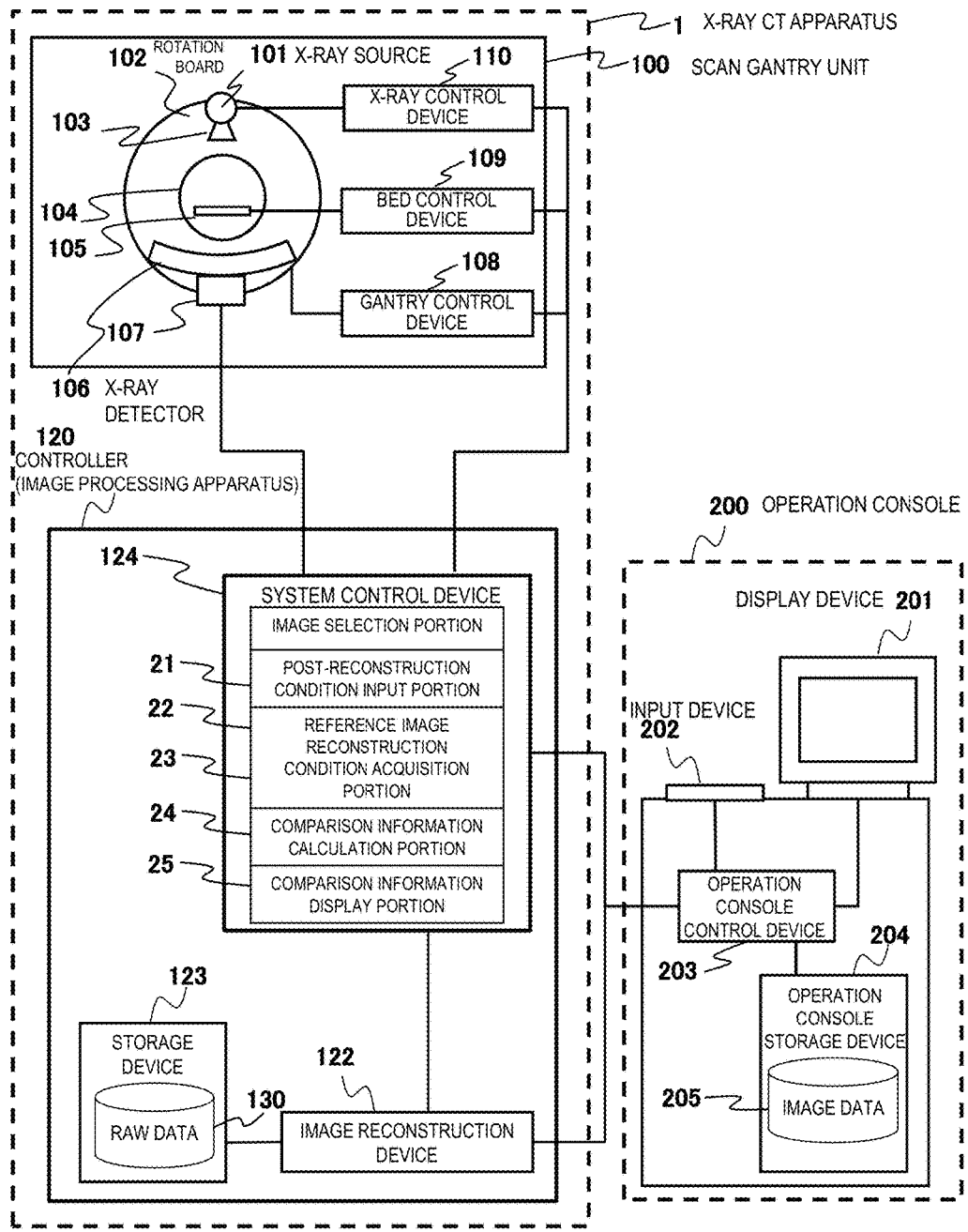
FIG. 1 is the entire configuration diagram of an X-ray CT apparatus 1 as an embodiment of an image processing apparatus according to the present invention.

As illustrated in FIG. 1, the X-ray CT apparatus 1 includes a scan gantry part (scan gantry unit) 100, a controller (an image processing apparatus or a control unit) 120, a bed 105, and an operation console 200.

The scan gantry unit 100 is a device which irradiates an object with X-rays and detects X-rays transmitted through the object. The control unit 120 is a device which controls each constituent element of the scan gantry unit 100, and acquires transmitted X-ray data measured by the scan gantry unit 100 so as to generate an image. The control unit 120 has a function of the image processing apparatus according to the present invention. The bed 105 is a device on which the object is laid and is mounted and which carries the object into and out of an X-ray irradiation range of the scan gantry unit 100. The operation console 200 is an input/output device which inputs various instructions to the scan gantry unit 100 and the control unit 120, and displays an image generated by an image reconstruction device 122. An operator inputs scanning conditions, reconstruction conditions, or the like via the operation console 200, and refers to an image displayed on a display device (display unit) 201.

The scan gantry unit 100 includes an X-ray source 101, a rotation board 102, a collimator 103, an X-ray detector 106, a data collecting device 107, a gantry control device 108, a bed control device 109, and an X-ray control device 110.

The control unit 120 includes the image reconstruction device 122, a system control device 124, and a storage device (storage unit) 123.

The operation console 200 includes the display device 201, an input device (input unit) 202, an operation console control device 203, and an operation console storage device 204, and is communicably connected to the control unit 120.

The rotation board 102 of the scan gantry unit 100 is provided with an opening 104, and the X-ray source 101 and the X-ray detector 106 are disposed to oppose each other with the opening 104 interposed therebetween. An object mounted on the bed 105 is inserted into the opening 104. The rotation board 102 is rotated around the object by a driving force which is transmitted from a rotation board driving device via a driving transmission system. The rotation board driving device is controlled by the gantry control device 108.

The X-ray source 101 is controlled by the X-ray control device 110 so as to apply X-rays with a predetermined intensity continuously or intermittently. The X-ray control device 110 controls an X-ray tube voltage applied to the X-ray source 101 and an X-ray tube current supplied thereto according to an X-ray tube voltage and an X-ray tube current determined by the system control device 124.

The collimator 103 is provided in an X-ray irradiation outlet of the X-ray source 101. The collimator 103 restricts an irradiation range of X-rays radiated from the X-ray source 101. For example, the X-rays are shaped into a cone beam (a conical beam or a pyramid-shaped beam). An aperture width of the collimator 103 is controlled by the system control device 124.

The X-rays, applied from the X-ray source 101, passing through the collimator 103, and transmitted through the object, are incident to the X-ray detector 106.

The X-ray detector 106 is a detector in which, for example, X-ray detection element groups each constituted of a scintillator and a photodiode are two-dimensionally arranged in a channel direction and a slice direction. The X-ray detector 106 is disposed to oppose the X-ray source 101 via the object. The X-ray detector 106 detects a dose of X-rays applied from the X-ray source 101 and transmitted through the object, and outputs the dose to the data collecting device 107.

The data collecting device 107 collects an X-ray dose detected by each X-ray detection element of the X-ray detector 106, converts the X-ray dose into digital data, and sequentially outputs the digital data to the image reconstruction device 122 of the control unit 120 as transmitted X-ray data.

The image reconstruction device 122 acquires the transmitted X-ray data which is input from the data collecting device 107, performs pre-processing such as logarithmic conversion and sensitivity correction on the data so as to generate projection data (raw data 130) which is necessary in reconstruction, and stores the data in the storage device 123. The image reconstruction device 122 applies preset reconstruction conditions to raw data 130 so as to reconstruct image data 205 regarding tomographic images or the like. The system control device 124 sends the image data 205 generated by the image reconstruction device 122 and the reconstruction conditions used when the image data 205 is reconstructed, to the operation console 200, and stores the data and the conditions in the operation console storage device 204. The system control device 124 displays the image data 205 on the display device 201.

FIG. 1 illustrates an example in which the storage devices 123 and 204 are respectively provided in the control unit 120 and the operation console 200, and the image data 205 and the raw data 130 are stored in the different storage devices 123 and 204, but the image data and the raw data may be stored in one storage device. The system control device 124, the image reconstruction device 122, and the storage device 123 of the control unit 120 illustrated in FIG. 1 may be provided on the operation console 200 side. In this case, the storage device 123 and the operation console storage device 204 may not necessarily be provided separately, and a single storage device may be provided.

The system control device 124 is a computer provided with a central processing unit (CPU), a read only memory (ROM), a random access memory (RAM), and the like. The system control device 124 transmits a control signal to each constituent element of the scan gantry unit 100, the control unit 120, and the operation console 200 of the X-ray CT apparatus 1 according to predetermined process procedures, so as to control scanning, image reconstruction, and input and output of various items of data.

Figure 2:
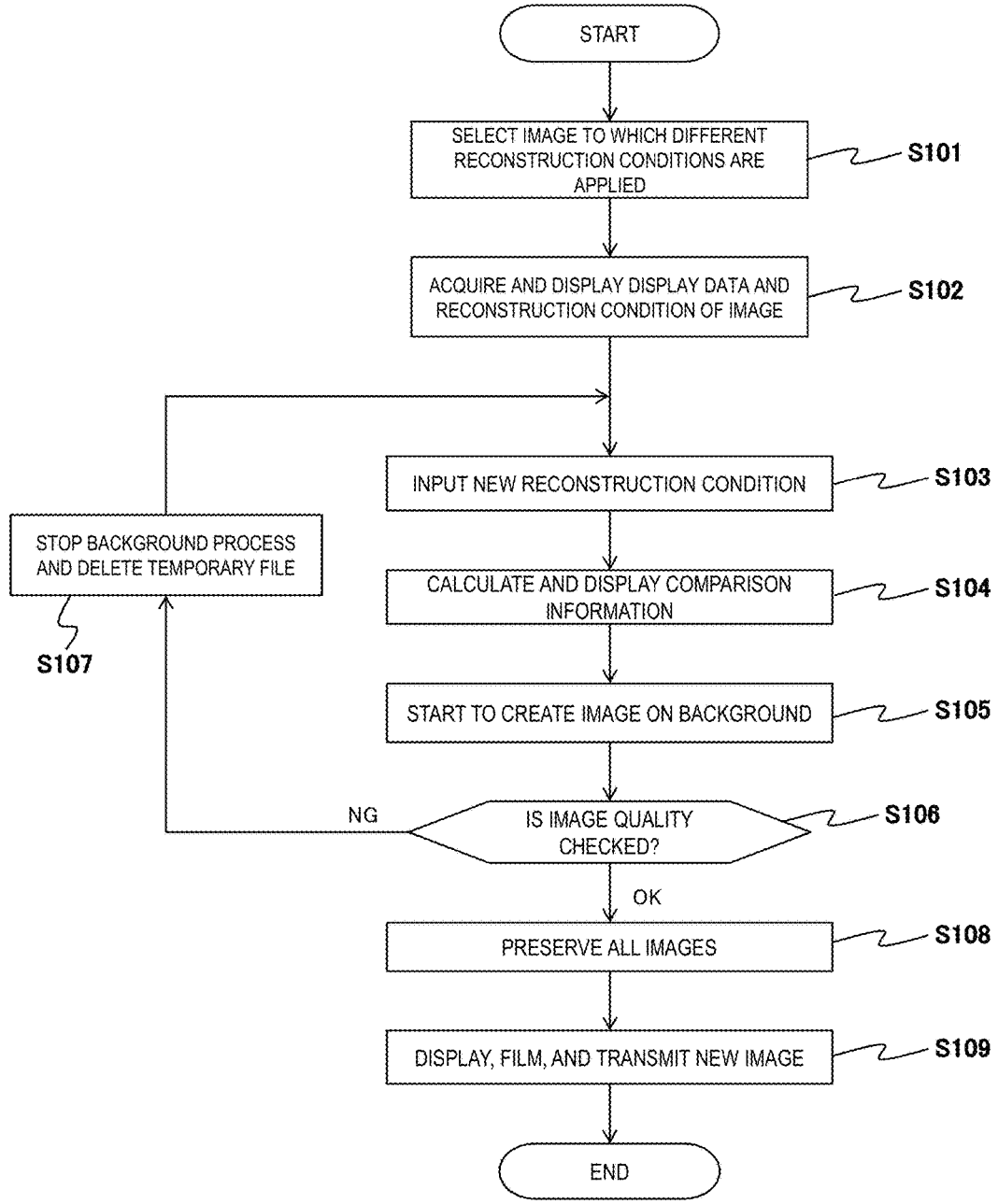
FIG. 2 is a flowchart illustrating procedures of an image reconstruction process performed by the X-ray CT apparatus 1.

The system control device 124 performs a reconstruction condition setting process according to process procedures illustrated in FIG. 2. Details of the reconstruction condition setting process will be described later.

The storage device 123 and the operation console storage device 204 are data recording devices such as hard disk drives. The storage device 123 stores the raw data 130 which is a base of the image data 205.

The operation console storage device 204 stores the image data 205 generated by the image reconstruction device 122. Additional information such as reconstruction conditions, patient information, examination information is typically stored in the same storage device (operation console storage device) 204 as the image data 205, but may be stored in the storage device 123 storing the raw data 130. The operation console storage device 204 stores in advance not only the above-described image data 205 or object information but also programs or data for realizing the function of the X-ray CT apparatus 1.

The operation console control device 203 is a computer including a CPU, a ROM, a RAM, and the like. The operation console control device 203 sends operations on the X-ray CT apparatus 1, various instructions and conditions, and the like, which are input from the input device 202, to the system control device 124 of the control unit 120. The operation console control device 203 displays the image data 205 or various items of display data on the display device 201 in response to an instruction sent from the system control device 124. The operation console control device 203 stores the image data 205 generated by the image reconstruction device 122 in the operation console storage device 204.

The display device 201 is constituted of a display device such as a liquid crystal panel or a CRT monitor, and a logic circuit for performing a display process in conjunction with the display device, and is connected to the operation console control device 203. The display device 201 displays an object image output from the image reconstruction device 122, and various information treated by the system control device 124.

The input device 202 is constituted of a pointing device such as a keyboard or a mouse, a numeric keypad, and various switch buttons, and outputs various instructions or information input by an operator, to the system control device 124 via the operation console control device 203. The operator operates the X-ray CT apparatus 1 in an interaction manner by using the display device 201 and the input device 202. The input device 202 may be a touch panel type input device which is integrally formed with a display screen of the display device 201.

Next, a functional configuration regarding reconstruction condition setting will be described.

The system control device 124 of the X-ray CT apparatus 1 includes, as the functional configuration regarding reconstruction condition setting, an image selection portion 21, a post-reconstruction condition input portion 22, a reference image reconstruction condition acquisition portion 23, a comparison information calculation portion 24, and a comparison information display portion 25 as illustrated in FIG. 1.

The post-reconstruction process is a process of reading the raw data 130 stored in the storage device 123, and reconstructing an image with reconstruction conditions which are different from reconstruction conditions set during scanning. In the following description, reconstruction conditions set during the post-reconstruction process will be referred to as "post-reconstruction conditions". An image reconstructed with reconstruction conditions set during scanning will be referred to as a "reference image" or an "original image", and reconstruction conditions used when the reference image is reconstructed will be referred to as "reference image reconstruction conditions".

The image selection portion 21 performs a process of selecting image data as a post-reconstruction processing target from among a plurality of items of image data 205 stored in the operation console storage device 204. The image data 205 is an image group including a plurality of sliced tomographic images obtained through examination (scanning) performed once in the X-ray CT apparatus 1. In the present embodiment, the image data 205 is stored in the operation console storage device 204, but, in a case where the image data 205 is stored in the storage device 123 of the control unit 120, the image selection portion 21 may select the image data 205 on which the post-reconstruction process will be performed, from the storage device 123 of the control unit 120.

The post-reconstruction condition input portion 22 receives post-reconstruction conditions which are input by the operator. In the post-reconstruction condition input process, the operation console control device 203 preferably displays, for example, a reconstruction condition setting screen 3 illustrated in FIG. 3, on the display device 201 as a user interface. The post-reconstruction condition input portion 22 sends post-reconstruction conditions which are input on the reconstruction condition setting screen 3 via the input device 202 by the operator, to the comparison information calculation portion 24.

The reference image reconstruction condition acquisition portion 23 uses one of the image data items (image group) selected by the image selection portion 21, as a reference image, and acquires reconstruction conditions stored in correlation with the reference image, from the operation console storage device 204 or the storage device 123. The comparison information calculation portion 24 is notified of the acquired reference image reconstruction conditions.

The comparison information calculation portion 24 calculates comparison information of image quality obtained in a case where an image is reconstructed with each condition on the basis of the reference image reconstruction conditions acquired by the reference image reconstruction condition acquisition portion 23 and the post-reconstruction conditions which are input via the post-reconstruction condition input portion 22. The comparison information calculation portion 24 preferably calculates the image quality as the comparison information on the basis of a modulation transfer function (MTF) of a reconstruction filter function and a value of each parameter included in the reference image reconstruction condition acquired by the reference image reconstruction condition acquisition portion 23 or the post-reconstruction conditions which are input via the post-reconstruction condition input portion 22.

The comparison information calculation portion 24 finishes calculation of comparison information before completing a post-reconstruction process of all images (all sliced images) of image data selected by the image selection portion 21. The comparison information preferably indicates to what extent various image quality index values such as image noise or contrast resolution become better or worse compared with the reference image after the post-reconstruction conditions are applied, by using graphics or numerical values.

Parameters which are taken into consideration when calculating the comparison information preferably include at least one of a field of view (FOV) size, an FOV center, a slice thickness, and a reconstruction filter function. When the comparison information is calculated, the comparison information calculation portion 24 calculates the entire comparison information by weighted-adding the obtained comparison information to each of the above-described parameter values.

A weight (contribution) applied to each parameter is preferably calculated in advance. Alternatively, the comparison information calculation portion 24 may generate an image quality index value indicating a difference between image quality obtained in a case where each parameter value is applied and image quality obtained in a case where a reference value is applied, as a table, hold the table in the storage device 123 or the like, read an image quality index value corresponding to a parameter value from the table for each parameter, and multiply the image quality index value by the parameter value.

Figure 3:
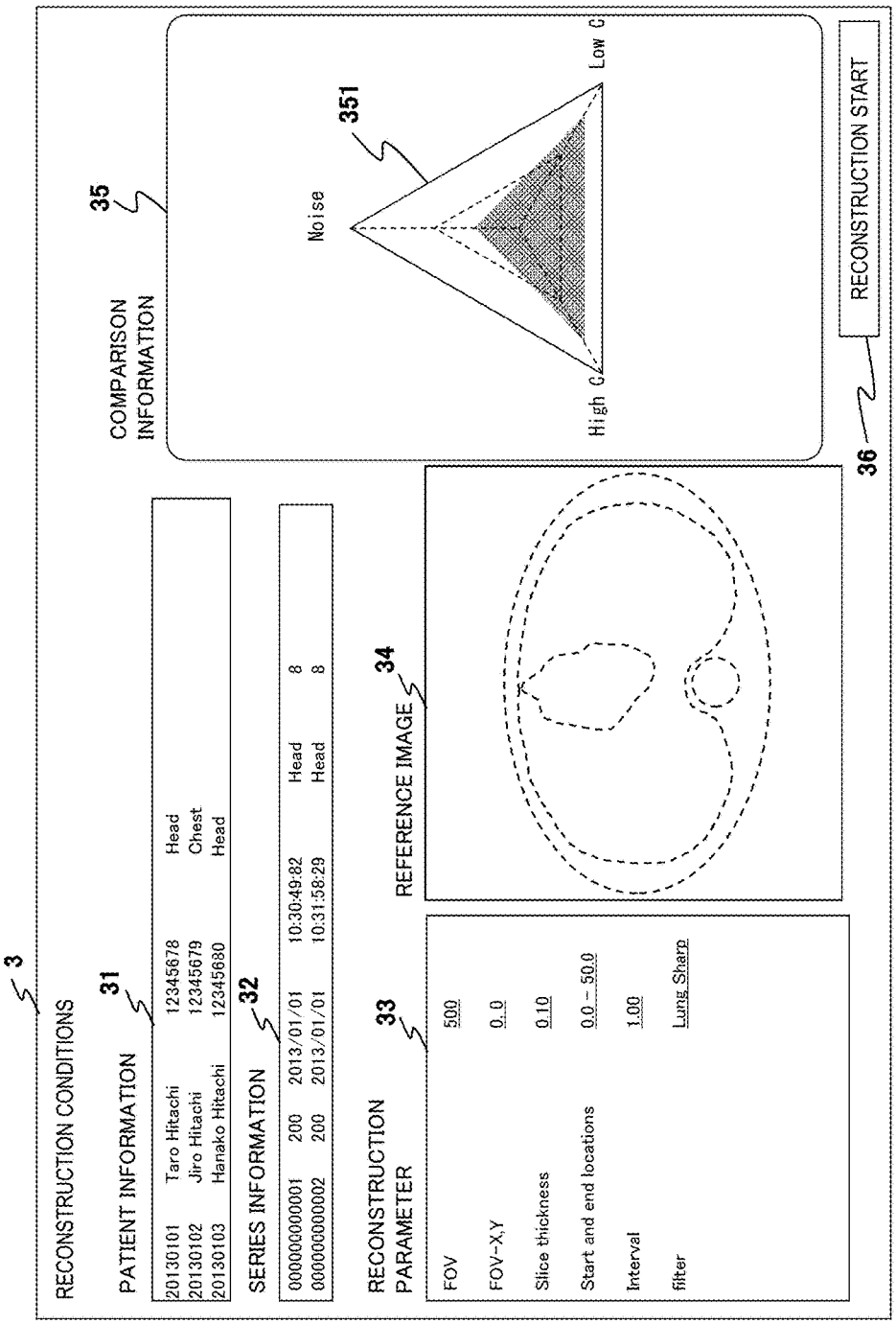
FIG. 3 illustrates an example of a reconstruction condition setting screen 3.

The comparison information display portion 25 displays the comparison information calculated by the comparison information calculation portion 24 on the display device 201 as illustrated in FIG. 3, for example. A display aspect of the comparison information will be described later.

Next, with reference to FIG. 2, a description will be made of procedures of the reconstruction condition setting process in the X-ray CT apparatus 1.

The system control device 124 of the X-ray CT apparatus 1 performs the reconstruction condition setting process according to procedures illustrated in the flowchart of FIG. 2. The system control device 124 reads a program and data regarding the reconstruction condition setting process from the operation console storage device 204, and performs the process on the basis of the program and the data.

This reconstruction condition setting process is assumed to be performed when a post-reconstruction process is performed on an image which has already been reconstructed, with separate reconstruction conditions. The reconstruction condition setting process is performed in a state in which image data (image group) reconstructed with certain reconstruction conditions is stored in the operation console storage device 204 or the like, and the reconstruction conditions used to reconstruct the image data or corresponding raw data 130 are stored in the operation console storage device 204 or the storage device 123.

In a scanning condition setting process, the system control device 124 of the X-ray CT apparatus 1 receives selection of a processing target image through the operator's operation (step S101). Display data (image data) of the selected image is acquired from the operation console storage device 204 as a reference image, and reconstruction conditions (reference image reconstruction conditions) applied to reconstruction of the image data is acquired from the operation console storage device 204. The acquired reference image or reference image reconstruction conditions are held in the RAM of the system control device 124 and are also displayed on the display device 201 (step S102).

The image selection process in step S101 or the process of displaying the selected image or the reconstruction conditions in step S102 is preferably performed by using, for example, the reconstruction condition setting screen 3 (user interface) illustrated in FIG. 3.

The reconstruction condition setting screen 3 illustrated in FIG. 3 will be described.

The reconstruction condition setting screen 3 is provided with a patient information display column 31, a series information display column 32, a reconstruction parameter input/display column 33, a reference image display column 34, a comparison information display column 35, a reconstruction start button 36, and the like.

The patient information display column 31 displays information such as patient information (the name, a patient ID, and the like), an image ID, examination information (the examination date and time, an examination ID, and the like), an examination part for each patient, for example, in a list form. If any examination or patient is selected by the operator from the patient information list displayed in the patient information display column 31, a list of image data regarding the selected examination or patient is generated by the system control device 124, and is displayed in the series information display column 32.

The series information display column 32 displays image data stored in correlation with examination information or patient information selected in the patient information display column 31, in a list form. Among image data items displayed in the series information display column 32, image data selected by the operator is a post-reconstruction processing target. A single sliced image in the selected image data is displayed in the reference image display column 34. As a reference image, any one of a plurality of images included in the selected image data may be used.

For example, a leading sliced image may be displayed in the reference image display column 34, and, more preferably, a representative image which will be described later may be displayed in the reference image display column 34. Preferably, the reference image displayed in the reference image display column 34 can be displayed in a switching manner in the slice direction. In other words, for example, if a forward operation or a rewind operation is input via the input device 202, slices of the reference image are preferably sequentially switched and displayed.

Consequently, the operator can display an image at a desired slice position in the reference image series in the reference image display column 34.

The reconstruction parameter input/display column 33 has respective input columns for editing values of the parameters of the reconstruction conditions. The parameters of the reconstruction conditions (post-reconstruction conditions) are a FOV size (FOV), a FOV center (FOV-X,Y), an image slice thickness (Slice thickness), a reconstruction range (Start and end location), a reconstruction interval (Interval), a reconstruction filter (filter), and the like. At an initial stage of reconstruction condition setting, the reconstruction conditions of the image data selected in step S102 are displayed in the reconstruction parameter input/display column 33. The operator inputs post-reconstruction conditions by changing a displayed numerical value of each parameter to any value.

The comparison information display column 35 is a display column which displays comparison information 351. The comparison information 351 represents a comparison result of image quality obtained in a case where an image is created by applying reconstruction conditions used when the reference image is reconstructed and in a case where an image is created by applying the post-reconstruction conditions which are input to the reconstruction parameter input/ display column 33. The comparison information 351 preferably relatively indicates to what extent each image quality index value of an image after a post-reconstruction process is performed becomes better or worse than that of the reference image. For example, the comparison information 351 may be represented in the form of a radar chart illustrated in FIG. 3 or other graphic forms, and a comparison result may be displayed in a numerical value such as "OO % improvement" or "XX % reduction".

In the example illustrated in FIG. 3, the comparison information 351 for image quality indexes of three types including image noise (Noise), high contrast resolution (High C), and low contrast resolution (Low C) is exemplified, but image quality indexes are not limited to three types, and the comparison information 351 for an image quality index of at least one type may be obtained. As the image quality indexes, indexes other than the image noise, the high contrast resolution, and the low contrast resolution may be used, and a comprehensive image quality evaluation value may be calculated on the basis of respective image quality index values. Calculation and display of the comparison information 351 will be described later in detail.

The reconstruction start button 36 is a button operated when a reconstruction process is started with the post-reconstruction conditions input to the reconstruction parameter input/display column 33. If the reconstruction start button 36 is pressed, the image reconstruction device 122 starts calculation of the comparison information 351 in the input post-reconstruction conditions, and also starts a post-reconstruction process on the background in parallel thereto.

The reconstruction start button 36 may function as a stop button of the reconstruction process during the post-reconstruction process. In other words, in a case where the currently performed post-reconstruction process is stopped, and new post-reconstruction conditions are desired to be applied, if the operator inputs separate post-reconstruction conditions and presses the "reconstruction start button 36" again, the image reconstruction device 122 stops the currently performed post-reconstruction process, and starts a post-reconstruction process with the new post-reconstruction conditions.

FIG. 2 is referred to again. If new reconstruction conditions (post-reconstruction conditions) are input to the reconstruction parameter input/display column 33 of the reconstruction condition setting screen 3 (step S103), the system control device 124 calculates comparison information on the basis of the original reconstruction conditions (reference image reconstruction conditions) and the post-reconstruction conditions input in step S103, and displays the comparison information 351 in the comparison information display column 35 (step S104). Calculation and display of the comparison information 351 will be described later.

The image reconstruction device 122 starts to create an image (post-reconstruction process) on the background in parallel to calculation and display of the comparison information 351 (step S105). The image creation process (post-reconstruction process) in step S105 is performed by applying the latest post-reconstruction conditions input in step S103. The image created in step S105 is stored in the RAM, the operation console storage device 204, or the like as a temporary file.

If the operator checks the comparison information 351 so as to check image quality after a post-reconstruction process, and inputs a reconstruction stopping instruction (step S106; NG), the system control device 124 stops the background process, and deletes the created temporary file (step S107). The system control device 124 proceeds to step S103, and receives input new post-reconstruction conditions.

Whenever new post-reconstruction conditions are input, the system control device 124 calculates the comparison information 351 on the basis of the original reconstruction conditions (reference image reconstruction conditions) and the latest post-reconstruction conditions input in step S103, and displays the comparison information 351 in the comparison information display column 35. An image reconstruction process is performed on the background (steps S103 to S105).

In a case where the operator checks the comparison information 351, and there is no problem in image quality (in a case where a reconstruction stopping instruction is not input) (step S106; OK), the system control device 124 continuously creates all sliced images (post-reconstruction process), and preserves all the created images in the operation console storage device 204 (step S108).

The images preserved in step S108 are displayed on the display device 201 as diagnosis images, filmed, or transmitted to an image viewing terminal communicably connected to the system control device (step S109).

Since the post-reconstruction process is performed as a background process, and the comparison information 351 is preferentially calculated and displayed, the operator can check in an early stage to what extent image quality of an image to which the post-reconstruction conditions are applied changes compared with the reference image by referring to the displayed comparison information 351.

A description will be made of calculation and display of the comparison information 351 in step S104.

The comparison information 351 is not calculated through comparison between images, but is obtained on the basis of reconstruction conditions and post-reconstruction conditions.

A description will be made of a method of obtaining comparison information with respect to image quality indexes such as (1) image noise, (2) high contrast resolution, and (3) low contrast resolution, as in the comparison information 351 illustrated in FIG. 3.

(1) Regarding Image Noise

Figure 4:
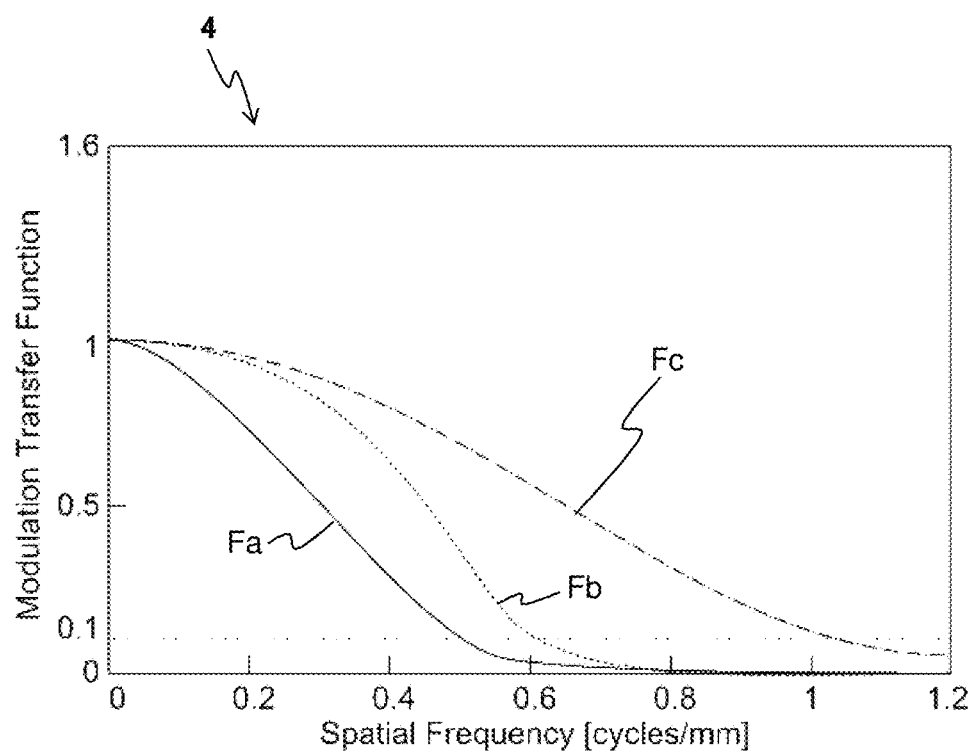
FIG. 4 is a diagram for explaining a modulation transfer function (MTF) used to calculate comparison information.

Parameters which influence image noise are mainly a reconstruction filter, an image slice thickness, and the like. Influence on image quality due to a difference in a reconstruction filter is obtained by using, for example, a modulation transfer function (MTF). The MTF is obtained by performing Fourier transform on a wire image in advance, and is an index for evaluating sharpness or a spatial resolution of an image on the basis of the extent of blurring. FIG. 4 is a diagram illustrating respective MTFs of reconstruction filter functions Fa, Fb and Fc, and a transverse axis of a graph 4 illustrated in FIG. 4 expresses a spatial frequency, and a longitudinal axis thereof expresses an MTF value. If an MTF value is great, a level of image noise also increases. In the example of the graph 4 illustrated in FIG. 4, an MTF value of the reconstruction filter function Fc is greater than MTF values of the reconstruction filter functions Fa and Fb. Thus, levels of image noise increase in the order of Fa<Fb<Fc. By comparing the MTF values with each other, image noise at each reconstruction filter function can be evaluated.

In relation to an image slice thickness, noise is reduced at a value indicating an appropriate thickness. A change amount (or a change ratio) of noise relative to a reference value for each image slice thickness value is obtained so as to be generated as a table in advance. The system control device 124 can calculate a comparison value of image noise due to a difference between image slice thicknesses by reading change amounts (or change ratios) of noise at respective image slice thicknesses in reference image reconstruction conditions and post-reconstruction conditions from the table and comparing the change amounts.

If the comparison value based on a difference in the reconstruction filter function and the comparison value based on a difference in the image slice thickness are obtained, the system control device 124 weighted-adds the obtained comparison values to each parameter. A weight (contribution to an image quality) applied to a parameter may be obtained in advance through phantom scanning.

Alternatively, in a case where the comparison values are expressed by change ratios, a comprehensive comparison value may be obtained by multiplying each parameter by the obtained comparison values.

(2) Regarding High Contrast Resolution

Parameters which influence a high contrast resolution include a reconstruction filter function, an FOV, a slice thickness, and the like. With respect to the reconstruction filter function, the above-described graph of the MTF which extends up to a high frequency causes a better high contrast resolution. In the example illustrated in FIG. 4, the reconstruction filter function Fc extends further toward a high frequency (the right direction on the transverse axis) than the reconstruction filter function Fb, and can thus be said to cause a better high contrast resolution. An MTF of each reconstruction filter function is held in advance, and the system control device 124 can calculate a comparison value of the high contrast resolution (High C) by comparing integral values of MTF values in high frequency regions of a reconstruction filter function of original reconstruction conditions and a reconstruction filter function of new reconstruction conditions (post-reconstruction conditions).

A CT image is formed of 512 pixels×512 pixels in a matrix, and thus a pixel pitch is FOV/512. Thus, as a value of the FOV becomes smaller, a resolution increases. As an image slice thickness becomes smaller, a width for combining CT values becomes narrower, and thus a boundary between different tissues is clear, thereby allowing a resolution to be improved. In the same manner as in the case of the above-described image noise, a change amount (or a change ratio) of the resolution relative to a reference value for each FOV value and for each image slice thickness value is obtained so as to be generated as a table in advance. The system control device 124 can calculate a comparison value of the high contrast resolution due to a difference between FOVs or image slice thicknesses by reading high contrast resolution change amounts (or change ratios) at respective FOV values or image slice thicknesses in reference image reconstruction conditions and post-reconstruction conditions from the table and comparing the change amounts.

Also in the high contrast resolution, in the same manner as in the case of the image noise, for example, a value indicating influence on image quality is weighted-added to each parameter. A weight (contribution to an image quality) applied to a parameter may be obtained in advance.

Alternatively, in a case where the comparison values are expressed by change ratios, a comprehensive comparison value may be obtained by multiplying each parameter by the obtained comparison values.

(3) Regarding Low Contrast Resolution

Parameters which influence a low contrast resolution include a reconstruction filter function, an image slice thickness, and the like. With respect to the reconstruction filter function, if an MTF value at a low frequency is close to 1.0, a smooth component is devotedly reproduced, and thus it may be determined that general contrast of an image is held. In the example illustrated in FIG. 4, the reconstruction filter function Fb has a greater value in the left low frequency region on the transverse axis than the reconstruction filter function Fa, and can thus be said to cause a higher low contrast resolution. Thus, an MTF of each reconstruction filter function is held in advance, and integral values of MTF values in low frequency regions of a reconstruction filter function of original reconstruction conditions and a reconstruction filter function of new reconstruction conditions (post-reconstruction conditions) are compared with each other. In relation to an image slice thickness, noise is reduced at a value indicating an appropriate thickness, and thus the low contrast resolution increases. A change in the low contrast resolution is calculated by using the reference image on the basis of such information.

Also in the low contrast resolution, in the same manner as in the case of the image noise or the high contrast resolution, for example, a comprehensive comparison value may be obtained by weighted-adding obtained comparison values to each parameter. A weight (contribution to an image quality) applied to a parameter may be obtained in advance.

Alternatively, in a case where the comparison values are expressed by change ratios, a comprehensive comparison value may be obtained by multiplying each parameter by the obtained comparison values.

The system control device 124 obtains a comparison value for each of the image quality indexes (the image noise, the high contrast resolution, and the low contrast resolution) according to the above-described method, and displays the values on a radar chart as illustrated in FIG. 3. The comparison information 351 illustrated in FIG. 3 is indicated by triangles having the image noise, the high contrast resolution, and the low contrast resolution as vertices. Assuming that an inner dashed line of a triangle represents 100% (image quality based on original reconstruction conditions), and an outer dashed line thereof represents, for example, 200%, a triangle of oblique lines represents to what extent image quality in each parameter becomes better or worse with a position of the dashed line as a reference. The comparison information 351 in FIG. 3 indicates that the image noise is reduced, and the high contrast resolution and the low contrast resolution are improved.

Figure 5:
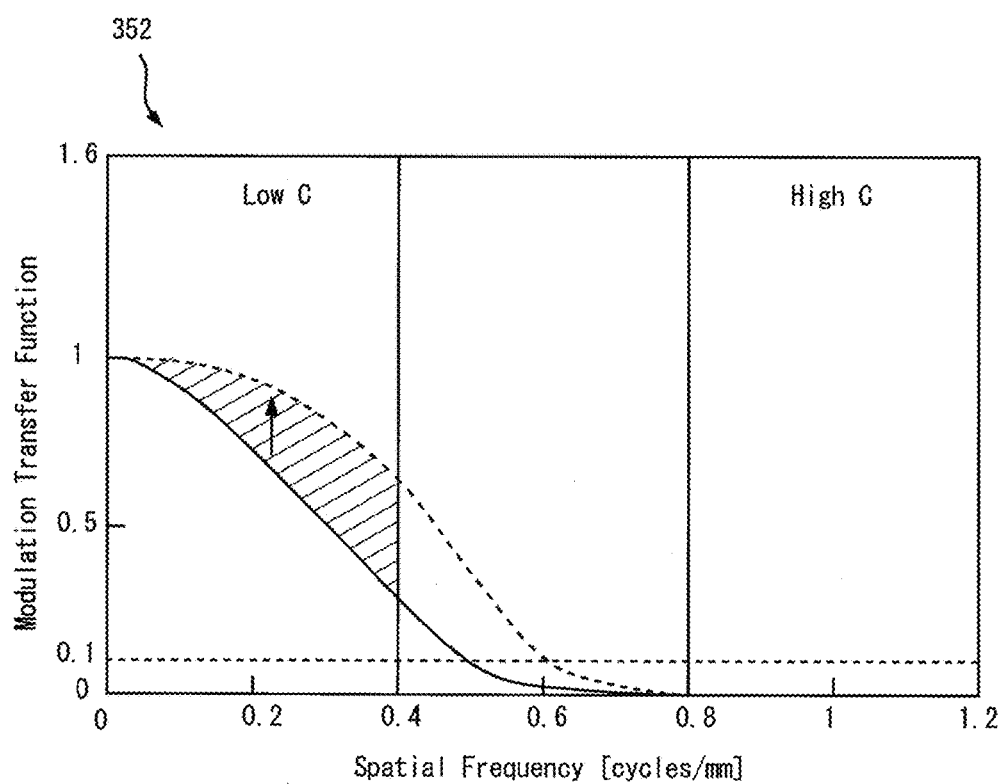
FIG. 5 illustrates another display example of comparison information.

An aspect of display of the comparison information 351 is not limited to the form of a radar chart as illustrated in FIG. 3. For example, comparison values obtained in the above-described comparison information calculation method may be displayed in numerical values. The numerical values may be displayed along with the comparison information 351 illustrated in FIG. 3. Alternatively, a comparison result of integral values of the MTFs may be displayed as comparison information 352 in a graph form illustrated in FIG. 5.

As described above, the image processing apparatus 120 of the first embodiment includes the control unit 120 that reconstructs images by using raw data measured by a medical imaging apparatus; the storage unit 123 that stores the raw data, the images, and reconstruction conditions used when the images are reconstructed, in correlation with each other; the display unit that displays an image read from the storage unit 123; and the input unit 202 that inputs selection of an image on which a post-reconstruction process will be performed among the images stored in the storage unit 123 and post-reconstruction conditions, by referring to the image displayed on the display unit, in which the control unit 120 receives selection of the image which is input via the input unit 202, reads selected image reconstruction conditions based on the received selection of the image from the storage unit 123, calculates comparison information of image quality on the basis of the read reconstruction conditions and post-reconstruction conditions input via the input unit 202, and displays the calculated comparison information on the display unit.

In other words, the reconstruction condition setting method of the first embodiment includes causing the image processing apparatus 120 to execute a step of reconstructing images by using raw data measured by a medical imaging apparatus; a step of storing the raw data, the images, and reconstruction conditions used when the images are reconstructed, in correlation with each other in the storage unit 123; a step of selecting an image on which a post-reconstruction process will be performed among the images stored in the storage unit 123; a step of inputting post-reconstruction conditions; a step of acquiring selected image reconstruction conditions from the storage unit 123; a step of calculating comparison information of image quality on the basis of the acquired reconstruction conditions and the input post-reconstruction conditions; and a step of displaying the calculated comparison information on a display unit.

As described above, the X-ray CT apparatus 1 of the first embodiment calculates and displays the comparison information 351 before creating an image when a post-reconstruction process is performed. Consequently, an operator can check to what extent quality of an image created after the post-reconstruction process is performed changes compared with a reference image, before creation of the image is completed. The comparison information 351 is obtained not through comparison between reconstructed images but on the basis of parameter values of reconstruction conditions, and can thus be calculated before an actual post-reconstruction process is performed. Consequently, the operator can check a change in image quality after the post-reconstruction process is performed, in an earlier stage than in the related art, and can thus rapidly perform reexamination or resetting of post-reconstruction conditions.

In the above-described procedures of the flowchart, a description has been made of an example in which the post-reconstruction process is performed as a background process in parallel to calculation of comparison information, but the procedures are only examples. For example, the post-reconstruction process may be started after the operator checks comparison information and inputs a reconstruction starting instruction.

Second Embodiment

Figure 6:
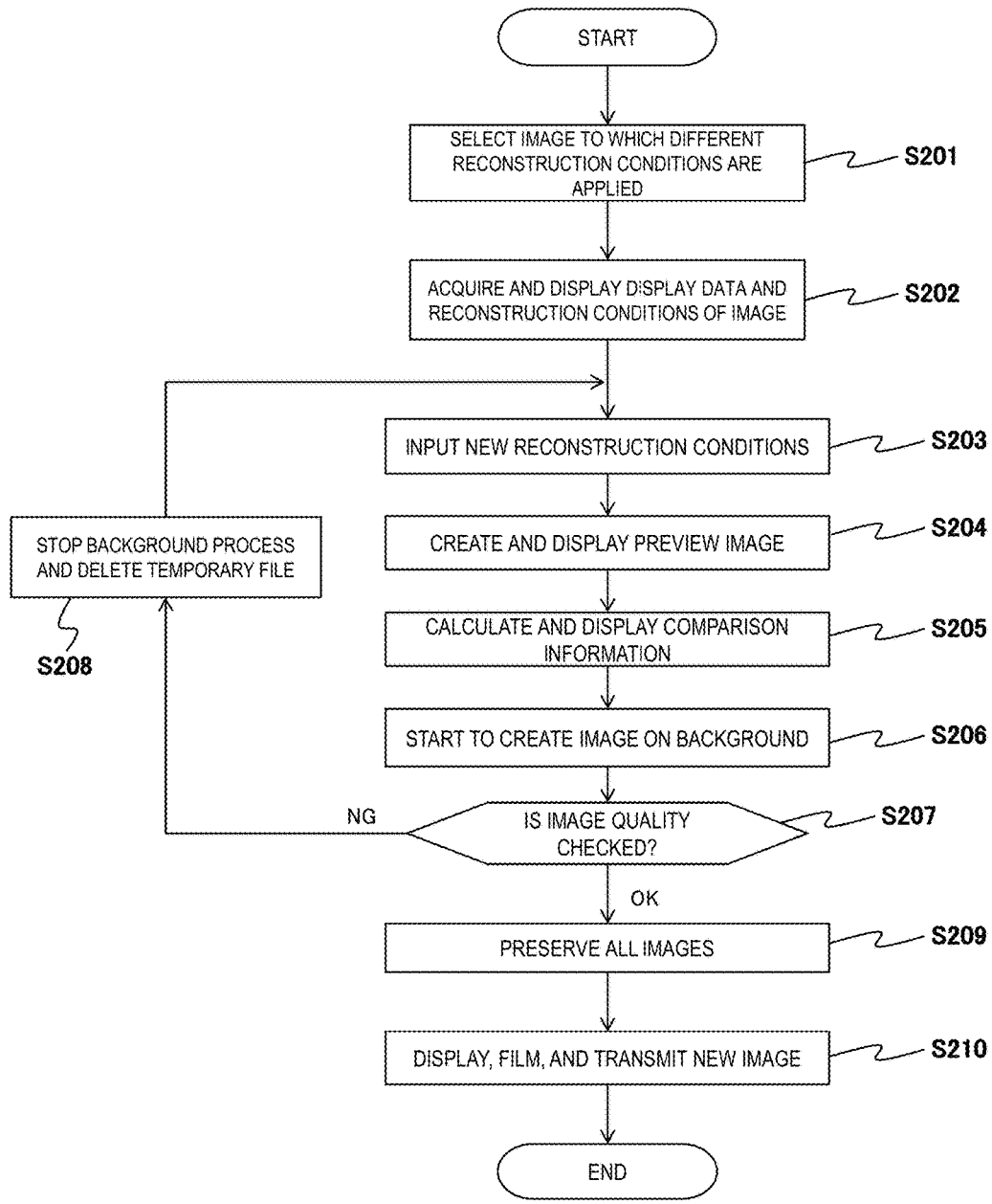
FIG. 6 is a flowchart illustrating procedures of an image reconstruction process performed by the X-ray CT apparatus 1 (second embodiment).

Next, with reference to FIGS. 6 and 7, a second embodiment of the present invention will be described.

In order to check image quality, preferably, not only the comparison information 351 but also an image obtained after an actual post-reconstruction process is performed can be referred to. However, it takes a long time to create all sliced images.

Therefore, in the second embodiment, in the same manner as in the first embodiment, the comparison information 351 is calculated and displayed, a representative sliced image (hereinafter, referred to as a representative image) of selected image data is subjected to a post-reconstruction process in new reconstruction conditions (post-reconstruction conditions), and thus a preview image 38 is generated and displayed. Images other than the representative image are subjected to the post-reconstruction process on the background in the same manner as in the first embodiment.

Hereinafter, with reference to FIG. 6, a description will be made of procedures of reconstruction condition setting process of the second embodiment.

Steps S201 to S203 are the same as steps S101 to S103 (FIG. 2) in the reconstruction condition setting process of the first embodiment. In other words, the system control device 124 of the X-ray CT apparatus 1 receives selection of a processing target image (an image to which different reconstruction conditions are applied) (step S201), acquires display data (reference image) of the selected image from the operation console storage device 204, and acquires corresponding raw data or reconstruction conditions used to reconstruct the image from the operation console storage device 204 or the storage device 123. The system control device 124 holds the acquired image data or reconstruction conditions in the RAM and also displays the data or the conditions on the display device 201 (step S202). The system control device 124 generates, for example, the reconstruction condition setting screen 3a as illustrated in FIG. 7, and receives input new reconstruction conditions (post-reconstruction conditions) (step S203).

If the post-reconstruction conditions are input, the system control device 124 creates and displays the preview image 38 (step S204).

The preview image 38 is an image reconstructed by applying the reconstruction conditions (post-reconstruction conditions) input in step S202, and is created on the basis of a representative image of image data.

The representative image is one sliced image of a plurality of sliced image data items. For example, a sliced image including feature points where a biological structure changes is preferably used as the representative image. In a case of an image of a blood vessel region, a sliced image including a blood vessel branching portion or a portion in which a CT value greatly changes is preferably used as the representative image. In order to determine a representative image, the system control device 124 may obtain, for example, an evaluation value indicating a feature point for each slice so as to generate a graph, and may obtain an inflection point thereof as a sliced image including feature points.

Alternatively, a central position of an attention part in a slice range may be obtained from a scanogram image which is a positioning image, and an image at the central position may be used as a representative image.

Alternatively, a representative image may be an image at the same slice position as that of an image displayed in the reference image display column 34.

The preview image 38 displayed in step S204 and the reference image 34 displayed in step S202 preferably have the same slice position. Therefore, a representative image is preferably determined in step S202.

Figure 7:
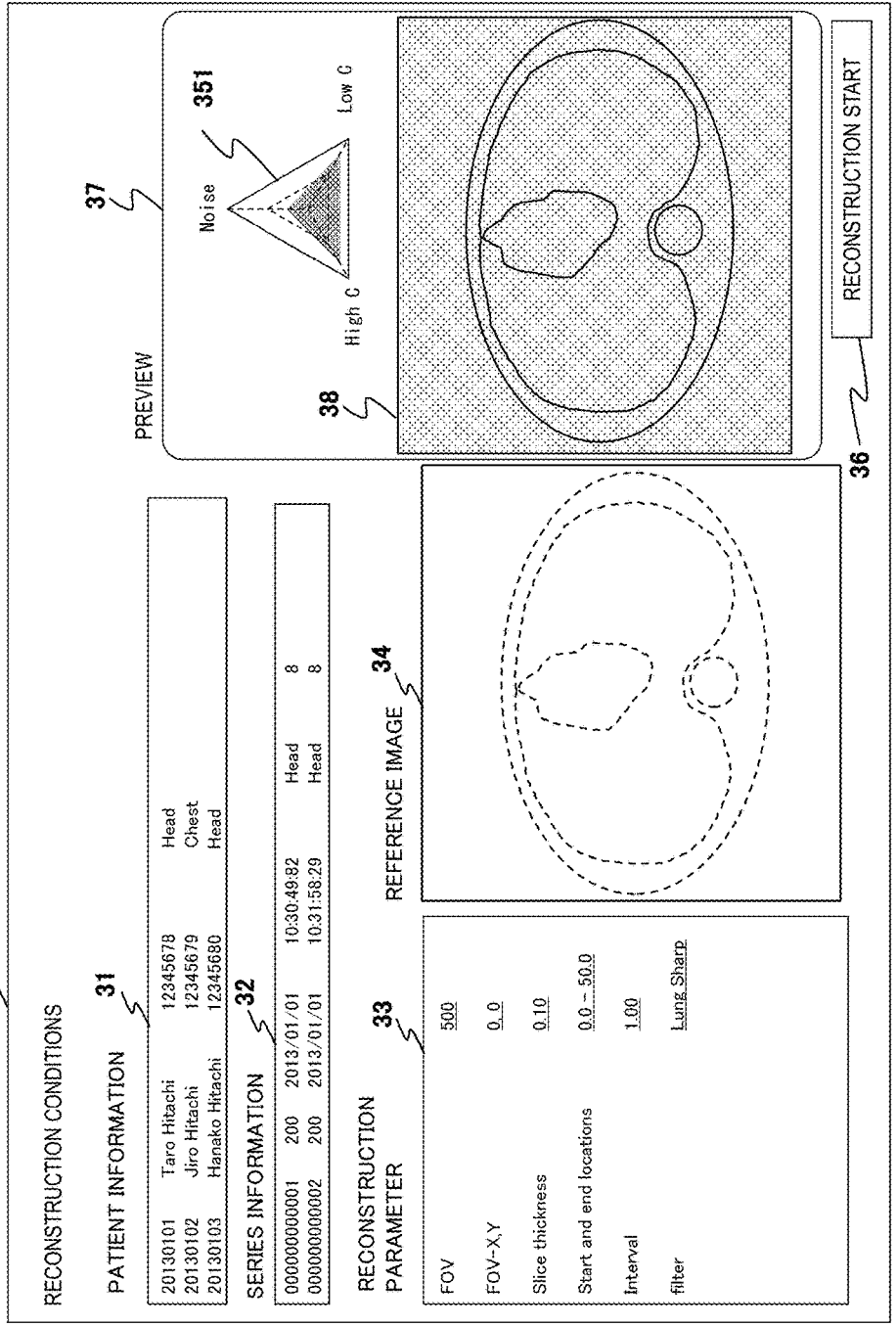

If the preview image 38 is created and displayed in step S204, the system control device 124 calculates the comparison information 351 on the basis of the original reconstruction conditions (reference image reconstruction conditions) and the new reconstruction conditions (post-reconstruction conditions) input in step S202, and displays the comparison information in a preview image display column 37 (step S205; refer to FIG. 7). Comparison information calculation and display processes are the same as those in the first embodiment.

The creation and display process of the preview image 38 (step S204) and the comparison information creation and display processes (step S205) may be changed in the orders thereof.

FIG. 7 illustrates an example of a reconstruction condition setting screen 3a in the second embodiment.

As illustrated in FIG. 7, the reconstruction condition setting screen 3a is different from the reconstruction condition setting screen 3 illustrated in FIG. 3 in that the preview image display column 37 is provided. The preview image display column 37 displays the preview image 38 reconstructed in step S204 and the comparison information 351 calculated in step S205.

Since the preview image to which the new reconstruction conditions (post-reconstruction conditions) are applied is displayed along with the comparison information 351 or the reference image 34 (an image based on the original reconstruction conditions), it becomes easier for the operator to recognize a change in image quality.

The operator checks a change in image quality before and after the conditions are changed by visually recognizing the displayed preview image 38 and comparison information 351 together, and the system control device 124 also starts image reconstruction on the background (step S206). The reconstruction process in step S206 is performed by applying the new reconstruction conditions (post-reconstruction conditions) input in step S203. The image created on the background is stored in the RAM, the operation console storage device 204, or the like as a temporary file.

If the operator checks image quality and inputs a reconstruction stopping instruction (step S207; NG), the system control device 124 stops the background process, and deletes the created temporary file (step S208). The system control device 124 proceeds to step S203, and receives input new reconstruction conditions.

Whenever new reconstruction conditions (post-reconstruction conditions) are input, the system control device 124 performs calculation of the preview image 38 and calculation of the comparison information 351 on the basis of the original reconstruction conditions (reference image reconstruction conditions) and the latest post-reconstruction conditions input in step S203, and displays the preview image 38 and the comparison information 351 in the preview image display column 37. A reconstruction process of images at slice positions other than the slice position of the preview image 38 is performed on the background (steps S203 to S206).

In a case where the operator checks image quality, and there is no problem in the image quality (in a case where a reconstruction stopping instruction is not input) (step S207; OK), the system control device 124 continuously creates all sliced images (post-reconstruction process), and preserves all the created images in the operation console storage device 204 (step S209).

The images preserved in step S209 are displayed on the display device 201 as diagnosis images, filmed, or transmitted to an image viewing terminal communicably connected to the system control device (step S210).

As described above, the image processing apparatus 120 of the second embodiment includes the control unit 120 that reconstructs images by using raw data measured by a medical imaging apparatus; the storage unit 123 that stores the raw data, the images, and reconstruction conditions used when the images are reconstructed, in correlation with each other; the display unit 201 that displays an image read from the storage unit 123; and the input unit 202 that inputs selection of an image on which a post-reconstruction process will be performed among the images stored in the storage unit 123 and post-reconstruction conditions, by referring to the image displayed on the display unit 201, in which the control unit 120 displays a preview image generated by the image reconstruction device 122 on the display unit 201, performs the post-reconstruction process on slices other than a slice of a representative image among selected images in parallel to generation and display of the preview image, performs the post-reconstruction process on the representative image among the selected images by applying the post-reconstruction conditions, generates the preview image by performing the post-reconstruction process, and displays the preview image on the display unit 201.

In other words, the reconstruction condition setting method of the second embodiment includes a step of reconstructing images by using raw data measured by a medical imaging apparatus; a step of storing the raw data, the images, and reconstruction conditions used when the images are reconstructed, in correlation with each other in the storage unit 123; a step of selecting an image on which a post-reconstruction process will be performed among the images stored in the storage unit 123; a step of inputting post-reconstruction conditions; a step of performing the post-reconstruction process by applying the post-reconstruction conditions to a representative image among selected images, so as to generate a preview image; a step of displaying the generated preview image; and a step of performing the post-reconstruction process on slices other than a slice of the representative image in parallel to generation and display of the preview image.

As mentioned above, in the second embodiment, prior to a post-reconstruction process of all images, the preview image 38 based on a representative image is created or the comparison information 351 is calculated, and is displayed. Thus, the operator refers to the preview image or the comparison information and can thus more easily recognize a change in image quality. Since a reconstruction process is performed on a preview image based on a representative image in image data including a plurality of images, it is possible to check image quality using the preview image without waiting for completion of the post-reconstruction process on all slices. The operator can decide whether to continuously perform the post-reconstruction process, or to stop the post-reconstruction process and input new reconstruction conditions, in an early stage.

Third Embodiment

Figure 8:
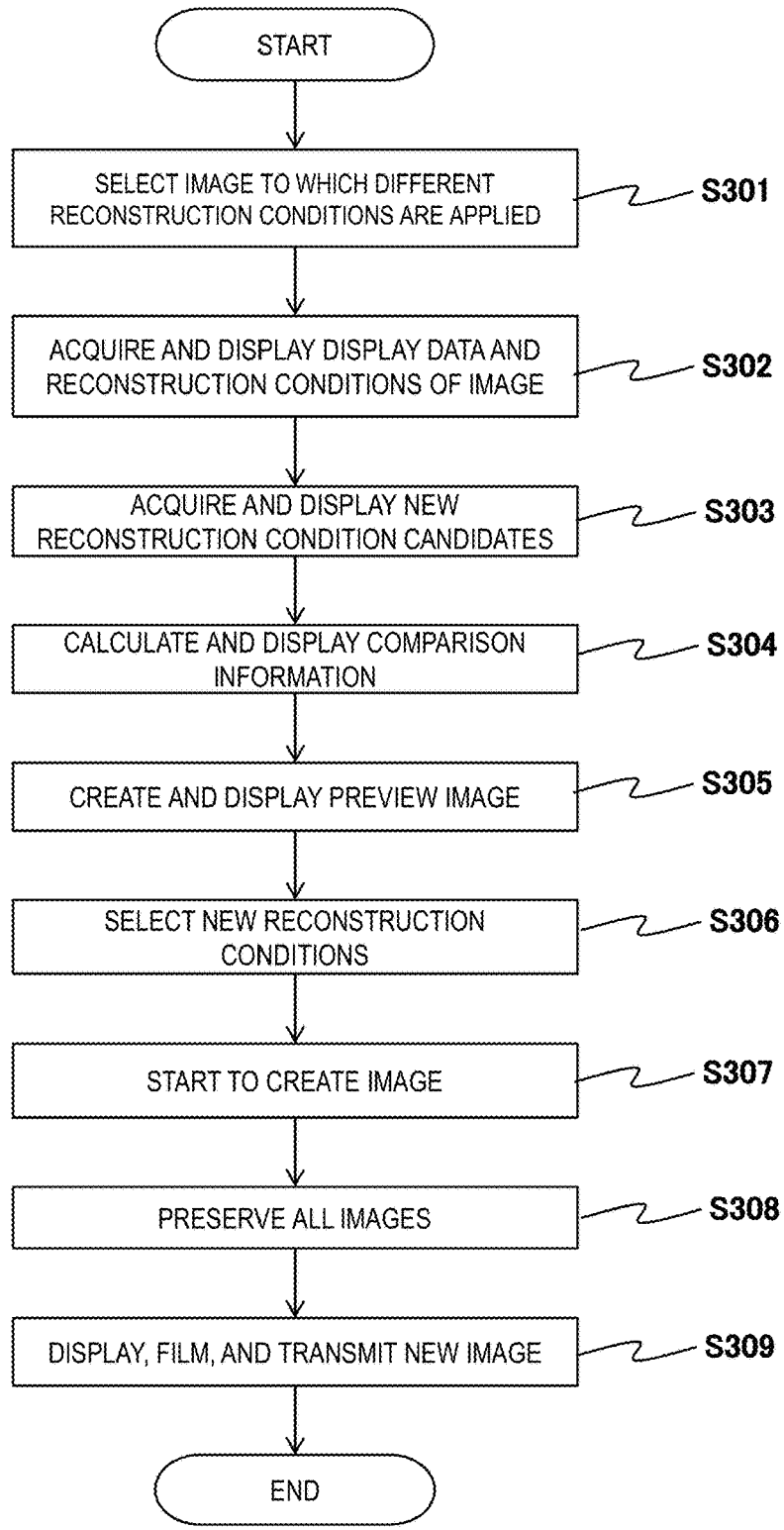
FIG. 8 is a flowchart illustrating procedures of an image reconstruction process performed by the X-ray CT apparatus 1 (third embodiment).

Next, with reference to FIG. 8, a third embodiment of the present invention will be described.

In order to obtain the optimum image quality, it is preferable to be capable of comparing image qualities in several reconstruction conditions (post-reconstruction conditions) with each other. Therefore, in the third embodiment, the system control device 124 presents a plurality of post-reconstruction condition candidates to an operator, calculates and displays comparison information for each post-reconstruction condition, and allows the user to perform selection. The operator determines a post-reconstruction condition by referring to the comparison information.

The X-ray CT apparatus 1 of the third embodiment holds a plurality of post-reconstruction condition candidates in the storage device 123 or the like in advance. As the post-reconstruction condition candidates, for example, a plurality of combinations of appropriate numerical values of respective parameters such as a FOV size, a FOV center, a slice thickness, a reconstruction range, a slice interval, and a reconstruction filter are assumed to be obtained and stored in advance. As the post-reconstruction condition candidates, a plurality of patterns are preferably stored for each examination part, or for each age or size of a patient.

Hereinafter, with reference to a flowchart of FIG. 8, a description will be made of a reconstruction condition setting process of the third embodiment.

The system control device 124 of the X-ray CT apparatus 1 receives selection of a processing target image through the operator's operation in the same manner as in the first embodiment (step S301). Display data (image data) of the selected image is acquired from the operation console storage device 204 as a reference image, and reconstruction conditions (reference image reconstruction conditions) applied to reconstruction of the image data is acquired from the operation console storage device 204. The system control device 124 holds the acquired reference image or reference image reconstruction conditions in the RAM and also displays the image or the conditions on the display device 201 (step S302).

Next, the system control device 124 reads a plurality of new reconstruction conditions (post-reconstruction conditions) candidates from the storage device 123 and displays the candidates on the display device 201 (step S303). In step S303, preferably, the system control device 124 narrows down and reads several post-reconstruction condition candidates from among the plurality of candidates stored in the storage device 123 on the basis of examination information or patient information related to the selected image.

The system control device 124 calculates comparison information with the original reconstruction conditions (reference image reconstruction conditions) for each post-reconstruction condition acquired in step S303, and displays the comparison information on the display device 201 (step S304). Calculation of the comparison information is the same as that in the first embodiment.

The system control device 124 creates a preview image to which each post-reconstruction condition acquired in step S303 is applied, and displays the preview image on the display device 201 (step S305). As described in the second embodiment, the preview image is preferably created by using, for example, a sliced image including feature points in the image data selected in step S301, as a representative image.

Through the processes in steps S301 to S305, the reference image, the plurality of post-reconstruction condition candidates, the preview images corresponding to the respective post-reconstruction condition candidates, and the comparison information are preferably displayed in an arranged manner on the display device 201. In a case where the whole information cannot be displayed due to restriction of a display screen size, for example, only the preview image corresponding to the respective candidates may be displayed without displaying a numerical value of each parameter of the post-reconstruction conditions, and only the comparison information may be displayed.

If the operator selects any one of the plurality of displayed post-reconstruction conditions (the comparison information, or the preview images) (step S306), the system control device 124 starts a post-reconstruction process on all slices by applying the selected post-reconstruction condition (step S307). The system control device 124 creates all sliced images (post-reconstruction process), and preserves all the created images in the operation console storage device 204 (step S308).

The images preserved in step S308 are displayed on the display device 201 as diagnosis images, filmed, or transmitted to an image viewing terminal communicably connected to the system control device (step S309).

As described above, according to the X-ray CT apparatus 1 of the third embodiment of the present invention, since comparison information or preview images related to a plurality of post-reconstruction condition candidates are calculated and displayed, the operator can check the optimum image quality and start a post-reconstruction process by referring to the comparison information or the preview images. The operator is not required to input each parameter of the post-reconstruction conditions, and can check states of image qualities corresponding to several candidates by using comparison information or preview images before starting the post-reconstruction process, and thus it is possible to smoothly set post-reconstruction conditions.

A post-reconstruction process may be started on the background before an image creating starting instruction is input. For example, a priority order may be set for a plurality of post-reconstruction condition candidates, and a post-reconstruction process may be performed in order from a post-reconstruction condition having the highest priority order. In this case, if the operator selects a post-reconstruction condition having a high priority order, all sliced images on which the post-reconstruction process was performed can be obtained more quickly. In a case where the operator selects a post-reconstruction condition which is different from a condition during execution of the post-reconstruction process, the background process may be stopped, the created temporary file may be deleted, and a post-reconstruction process may be performed on all images by using the selected post-reconstruction condition.

Fourth Embodiment

Next, with reference to FIG. 9, a fourth embodiment of the present invention will be described.

In the fourth embodiment, the system control device 124 omits the comparison information calculation and display processes (step S205) from the flow of the reconstruction condition setting process (FIG. 6) in the second embodiment, and generates and displays a preview image based on a representative image. A post-reconstruction process is performed on images other than the representative image on the background while the operator visually recognizes the preview image and checks image quality.

In other words, the system control device 124 of the X-ray CT apparatus 1 receives selection of a processing target image (an image to which different reconstruction conditions are applied) by an operation of the operator, acquires display data of the selected image, and acquires reconstruction conditions applied to reconstruction of the image data from the operation console storage device 204. The acquired reconstruction conditions are held in the RAM and is also displayed on the display device 201.

FIG. 9 illustrates an example of a reconstruction condition setting screen 3b in the fourth embodiment.

As illustrated in FIG. 9, the reconstruction condition setting screen 3b is different from the reconstruction condition setting screen 3 illustrated in FIG. 3 in that the preview image 38 is displayed, and comparison information or a reference image is not displayed.

For example, if new reconstruction conditions (post-reconstruction conditions) are input to the reconstruction parameter input/display column 33 of the reconstruction condition setting screen 3b illustrated in FIG. 9, the system control device 124 receives the input post-reconstruction conditions, applies the post-reconstruction conditions so as to create the preview image 38, and displays the preview image 38 on the reconstruction condition setting screen 3b. The preview image 38 is created on the basis of a representative image in processing target image data in the same manner as in the second embodiment.

The system control device 124 starts image reconstruction on the background while the operator checks image quality after the conditions are changed by visually recognizing the displayed preview image 38. This reconstruction process is performed by applying the new reconstruction conditions (post-reconstruction conditions). The image created on the background is stored in the RAM, the operation console storage device 204, or the like as a temporary file.

If the operator checks image quality on the basis of the preview image 38, and inputs a reconstruction stopping instruction, the system control device 124 stops the background process, deletes the created temporary file, and receives input new reconstruction conditions.

When new reconstruction conditions are input, the system control device 124 creates and displays the preview image 38 on the basis of the new reconstruction conditions. An image reconstruction process is performed on the background.

In a case where there is no problem in the image quality of the preview image 38 (in a case where a reconstruction stopping instruction is not input), the system control device 124 continuously creates all sliced images (post-reconstruction process), and preserves all the created images in the operation console storage device 204.

As described above, according to the fourth embodiment, if new reconstruction conditions are input, the preview image 38 based on a representative image is created and displayed, and a post-reconstruction process is started on the background. Even if comparison information is not calculated, the operator can check actual image quality by using an image at early timing by visually recognizing the preview image 38. An amount of display information is small, and thus a configuration of the screen can be simplified.

Fifth Embodiment

Next, with reference to FIG. 10, a fifth embodiment of the present invention will be described.

In the first to fourth embodiments, the operation console 200 of the X-ray CT apparatus 1 performs inputting of an operation or display of comparison information or the like, but the present invention is not limited thereto, and reconstruction conditions may be set by using an operation terminal which is remotely disposed and is communicably connected to the X-ray CT apparatus via a network.

Figure 10:
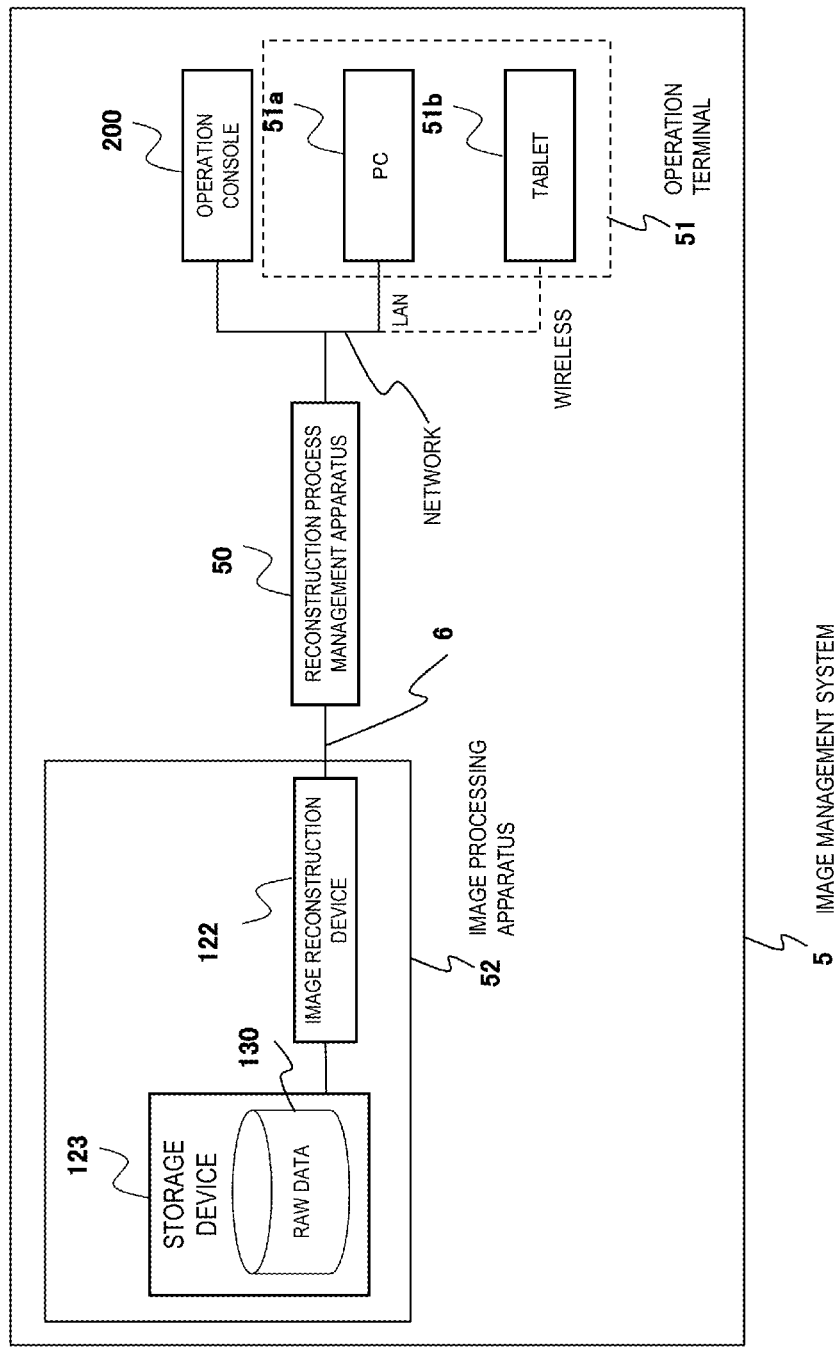
FIG. 10 is the entire configuration diagram of an image management system 5 which performs an image reconstruction process in response to instructions from a plurality of operation terminals 51.

FIG. 10 is a diagram illustrating the entire configuration of an image management system 5.

In the image management system 5, an image processing apparatus 52 according to the present invention is communicably connected to a reconstruction process management apparatus 50 and an operation terminal 51 via a network 6. The network 6 may include, for example, a local area network (LAN) disposed in a medical facility, or a wider network. The network 6 may be a wireless or wired network.

The operation terminal 51 is a computer having the same function as that of the operation console 200 illustrated in FIG. 1, and includes various electronic apparatuses such as a personal computer (PC) 51a or a tablet PC 51b provided with a display device, an input device, a control device, a storage device, and a communication interface. The operation terminal 51 (the PC 51a or the tablet PC 51b) inputs various instructions for the image processing apparatus 52, and transmits the instructions to the reconstruction process management apparatus 50 via the network 6.

The reconstruction process management apparatus 50 transmits the received instructions to the image processing apparatus 52 via the network 6. The operation terminal 51 receives an image or display data generated by the image reconstruction device 122 of the image processing apparatus 52 via the reconstruction process management apparatus 50, and displays the image or the display data on the display device of the operation terminal 51.

The image processing apparatus 52 is, for example, a medical imaging apparatus such as the X-ray CT apparatus 1 or an image processing computer which reconstructs (performs post-reconstruction on) an image( ). The image reconstruction device 122 illustrated in FIG. 10 performs the reconstruction condition setting process in the first to fourth embodiments in response to an instruction which is input from the operation terminal 51 via the reconstruction process management apparatus 50. The image processing apparatus 52 includes the image selection portion 21, the post-reconstruction condition input portion 22, the reference image reconstruction condition acquisition portion 23, the comparison information calculation portion 24, the comparison information display portion 25, and the like, in the same manner as the system control device 124 illustrated in FIG. 1, and creates display data of the reconstruction condition setting screen 3, 3a or 3b, calculates the comparison information 351, or generates the preview image 38 in response to a processing request from the reconstruction process management apparatus 50. A processing result in the image processing apparatus 52 is transmitted to the operation terminal 51 which is a request source, via the reconstruction process management apparatus 50 at any time.

The reconstruction process management apparatus 50 is a computer which manages a reconstruction request source or a queue process. If a plurality of operation terminals 51 make reconstruction process requests, a plurality of requests may overlap each other. Thus, time required to complete reconstruction of all images greatly increases. Therefore, the reconstruction process management apparatus 50 is provided in the image management system 5, performs a process such as distribution of created data or allocation of priority of a response with respect to process requests from the plurality of operation terminals 51, and determines processing order. A process starting request is transmitted to the image processing apparatus 52 in the determined order.

In the reconstruction condition setting process, the reconstruction process management apparatus 50 transmits a signal or a process request which is input from the operation terminal 51, to the image processing apparatus 52, or transmits display data or the like which is input from the image processing apparatus 52, to the operation terminal 51.

For example, if an instruction for starting the reconstruction condition setting process is received from the operation terminal 51, the image processing apparatus 52 generates the reconstruction condition setting screen 3 illustrated in FIG. 3 on the basis of raw data, patient information, or examination information stored in the storage device 123, and transmits the reconstruction condition setting screen to the operation terminal 51. If an instruction signal for an image (reference image) selected on the operation terminal 51 side is received, display data of the reference image is read in response to the received instruction signal, and is transmitted to the operation terminal 51. Calculation of comparison information based on reference image reconstruction conditions and post-reconstruction conditions, or a post-reconstruction process on the background is performed in predetermined order in response to an instruction from the reconstruction process management apparatus 50, and a processing result is returned to the reconstruction process management apparatus 50. The reconstruction process management apparatus 50 transmits the processing result to the operation terminal 51 which is a request source.

As described above, in the image management system 5 of the fifth embodiment, an operation of the same the reconstruction condition setting process as in the first to fourth embodiments can be input or a result can be returned to the operation terminal 51 so as to be displayed, in response to instructions from a plurality of operation terminals 51 which are connected via the network 6. Since the reconstruction process management apparatus 50 performs a process such as distribution of created data or allocation of priority so as to manage a reconstruction request source or to manage a queue process, comparison information or a preview image can be smoothly calculated in the image processing apparatus 52 so as to be returned to the operation terminal 51 which is a request source.

In the example illustrated in FIG. 10, a single image processing apparatus 52 is connected to the reconstruction process management terminal 50, but a plurality of image processing apparatuses 52 having the same function may be connected thereto. In this case, calculation of comparison information or a post-reconstruction process performed on the background can be distributed to the plurality of image processing apparatuses 52 so as to be performed, and thus it is possible to obtain processing results more rapidly.

Other Aspects of Each Embodiment

The control unit 120 may apply the post-reconstruction conditions to a representative image among selected images so as to perform a post-reconstruction process and to generate a preview image, and may display the preview image on the display unit along with the comparison information.

The control unit 120 may use, as the representative image, an image at a body axis direction position corresponding to the center of a part or an image at a body axis direction position including a feature point where a structure changes.

The control unit 120 may calculate the comparison information on the basis of a value of at least one of a modulation transfer function of a reconstruction filter function and each parameter included in the reconstruction conditions or the post-reconstruction conditions.

The control unit 120 may complete calculation of the comparison information before performing post-reconstruction on all sliced images included in selected images.

The control unit 120 may apply the post-reconstruction conditions to a representative image among selected images so as to perform a post-reconstruction process and to generate a preview image based on the representative image subjected to the post-reconstruction process, and may perform the post-reconstruction process on sliced images other than the representative image in parallel to calculation and display of the comparison information after generating the preview image.

In a case where post-reconstruction conditions which are different from the post-reconstruction conditions are input or an instruction for stopping a post-reconstruction process on sliced images other than the representative image is input via the input device 202, the control unit 120 may regard the input instruction as stoppage of currently performed the post-reconstruction process, and, in a case where the different post-reconstruction conditions are input, the control unit may calculate comparison information between the received different post-reconstruction conditions and the reconstruction conditions.

As mentioned above, the preferred embodiments of the image processing apparatus according to the present invention have been described, but the present invention is not limited to the above-described embodiments. It is clear that a person skilled in the art can conceive of various modifications or alterations within the technical spirit disclosed in the present specification, and it is understood that they are naturally included in the technical scope of the present invention.

REFERENCE SIGNS LIST

1 X-ray CT apparatus, 100 scan gantry unit, 120 image processing apparatus (control unit, controller), 122 image reconstruction device, 123 storage device (storage unit), 124 system control device, 130 raw data, 200 operation console, 201 display device (display unit), 202 input device (input unit), 203 operation console control device, 204 operation console storage device, 205 image data, 21 image selection portion, 22 post-reconstruction condition input portion, 23 reference image reconstruction condition acquisition portion, 24 comparison information calculation portion, 25 comparison information display portion, 3, 3a and 3b reconstruction condition setting screen, 351 and 352 comparison information, 38 preview image, 5 image management system, 50 reconstruction process management apparatus, 51 operation terminal, 52 image processing apparatus, 6 network

The invention claimed is:

1. An image processing apparatus comprising:
   a control unit that reconstructs images by using raw data measured by a medical imaging apparatus;
   a storage unit that stores the raw data, the images, and reconstruction conditions used when the images are reconstructed, in correlation with each other;
   a display unit that displays an image read from the storage unit; and
   an input unit that inputs selection of an image on which a post-reconstruction process will be performed among the images stored in the storage unit and post-reconstruction conditions, by referring to the image displayed on the display unit,
   wherein the control unit receives selection of the image which is input via the input unit, reads the selected image reconstruction conditions from the storage unit, calculates comparison information of image quality obtained in a case where an image is reconstructed with each condition on the basis of the read reconstruction conditions and post-reconstruction conditions input via the input unit, and displays the calculated comparison information on the display unit.

2. The image processing apparatus according to claim 1, wherein the control unit applies the post-reconstruction conditions to a representative image among selected images so as to perform the post-reconstruction process and to generate a preview image, and displays the preview image on the display unit along with the comparison information.

3. The image processing apparatus according to claim 2, wherein the control unit uses, as the representative image, an image at a body axis direction position corresponding to the center of a part or an image at a body axis direction position including a feature point where a structure changes.

4. The image processing apparatus according to claim 1, wherein the control unit calculates the comparison information on the basis of a value of at least one of a modulation transfer function of a reconstruction filter function and each parameter included in the reconstruction conditions or the post-reconstruction conditions.

5. The image processing apparatus according to claim 1, wherein the control unit completes calculation of the comparison information before performing the post-reconstruction process on all sliced images included in the selected images.

6. The image processing apparatus according to claim 1, wherein the control unit applies the post-reconstruction conditions to a representative image among selected images so as to perform the post-reconstruction process and to generate a preview image based on the representative image subjected to the post-reconstruction process, and performs the post-reconstruction process on sliced images other than the representative image in parallel to calculation and display of the comparison information after generating the preview image.

7. The image processing apparatus according to claim 6, wherein, in a case where post-reconstruction conditions which are different from the post-reconstruction conditions are input or an instruction for stopping the post-reconstruction process on sliced images other than the representative image is input via the input unit, the control unit regards the input as an instruction for stopping the currently performed post-reconstruction process, and, in a case where the different post-reconstruction conditions are input, the control unit calculates comparison information between the received different post-reconstruction conditions and the reconstruction conditions.

8. An image processing apparatus comprising:
   a control unit that reconstructs images by using raw data measured by a medical imaging apparatus;
   a storage unit that stores the raw data, the images, and reconstruction conditions used when the images are reconstructed, in correlation with each other;
   a display unit that displays an image read from the storage unit; and
   an input unit that inputs selection of an image on which a post-reconstruction process will be performed among the images stored in the storage unit and post-reconstruction conditions, by referring to the image displayed on the display unit,
   wherein the control unit receives selection via the input unit of an original image which was constructed using the raw data and reconstruction conditions, reads the selected original image reconstruction conditions from the storage unit, calculates comparison information of image quality between the original image and an output scheduled image reconstructed using a same said raw data and a changing of the reconstruction conditions to the post-reconstruction conditions input via the input unit, and displays the calculated comparison information on the display unit.

9. A reconstruction condition setting method comprising:
   reconstructing images by using raw data measured by a medical imaging apparatus;
   storing the raw data, the images, and reconstruction conditions used when the images are reconstructed, in correlation with each other in the storage unit;
   selecting an image on which a post-reconstruction process will be performed among the images stored in the storage unit;
   inputting post-reconstruction conditions;
   acquiring selected image reconstruction conditions from the storage unit;
   calculating comparison information of image quality obtained in a case where an image is reconstructed with each condition on the basis of the acquired reconstruction conditions and the input post-reconstruction conditions; and
   displaying the calculated comparison information.

* * * * *